United States Patent
Kang

(10) Patent No.: US 11,058,209 B2
(45) Date of Patent: Jul. 13, 2021

(54) BEAUTY COUNSELING INFORMATION PROVIDING DEVICE AND BEAUTY COUNSELING INFORMATION PROVIDING METHOD

(71) Applicant: LG ELECTRONICS INC., Seoul (KR)

(72) Inventor: Shin Jae Kang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 11 days.

(21) Appl. No.: 16/600,301

(22) Filed: Oct. 11, 2019

(65) Prior Publication Data

US 2020/0037732 A1 Feb. 6, 2020

(30) Foreign Application Priority Data

Aug. 16, 2019 (KR) .......................... 10-2019-0100132

(51) Int. Cl.
*G06K 9/00* (2006.01)
*A45D 44/00* (2006.01)
(Continued)

(52) U.S. Cl.
CPC .......... *A45D 44/005* (2013.01); *G06K 9/6202* (2013.01); *G06K 9/6267* (2013.01);
(Continued)

(58) Field of Classification Search
CPC ........... A45D 2044/007; A45D 44/005; G06K 9/00281; G06K 9/00369; G06K 9/00671;
(Continued)

(56) References Cited

U.S. PATENT DOCUMENTS

2003/0065278 A1* 4/2003 Rubinstenn .......... A61B 5/0062
600/587
2007/0036456 A1* 2/2007 Hooper ................... G06T 5/008
382/274
(Continued)

FOREIGN PATENT DOCUMENTS

EP 1 297 782 A1 4/2003
EP 3 249 562 A1 11/2017
(Continued)

OTHER PUBLICATIONS

Aronne, "Classification of Obesity and Assessment of Obesity-Related Health Risk", Obesity Research, vol. 10, No. S2, Dec. 1, 2002, pp. 105S-115S, XP55712288.
(Continued)

*Primary Examiner* — Xin Jia
(74) *Attorney, Agent, or Firm* — Birch, Stewart, Kolasch & Birch, LLP

(57) ABSTRACT

Disclosed is a beauty counseling information providing method and apparatus, which may generate and provide beauty counseling information by executing an artificial intelligence (AI) algorithm and/or a machine learning algorithm in a 5G environment connected for Internet-of-Things. A beauty counseling information providing method according to an embodiment of the present disclosure may include generating a first image set that has classified a plurality of images previously stored based on capturing information every predetermined period, generating a second image set that has classified a plurality of images included in the first image set based on the purpose of providing counseling information, calculating a body feature through comparative analysis of the plurality of images included in the second image set, and providing the beauty counseling information when the amount of change between the calculated body
(Continued)

feature and previously stored existing body feature exceeds a predetermined value.

14 Claims, 6 Drawing Sheets

(51) Int. Cl.
    *G06T 7/00*     (2017.01)
    *G06T 7/11*     (2017.01)
    *G06T 7/13*     (2017.01)
    *G06K 9/62*     (2006.01)
    *G06T 7/174*     (2017.01)

(52) U.S. Cl.
    CPC .............. *G06T 7/0012* (2013.01); *G06T 7/11* (2017.01); *G06T 7/13* (2017.01); *G06T 7/174* (2017.01); *A45D 2044/007* (2013.01); *G06T 2207/30088* (2013.01); *G06T 2207/30201* (2013.01)

(58) Field of Classification Search
    CPC ................ G06K 9/6202; G06K 9/6267; G06T 2200/24; G06T 2207/10024; G06T 2207/30088; G06T 2207/30196; G06T 2207/30201; G06T 7/0012; G06T 7/0016; G06T 7/11; G06T 7/13; G06T 7/174; G16H 30/40; G16H 50/20
    See application file for complete search history.

(56) References Cited

U.S. PATENT DOCUMENTS

| | | | |
|---|---|---|---|
| 2008/0125289 A1 | 5/2008 | Pryor et al. | |
| 2019/0213452 A1* | 7/2019 | Ludwinski | G06T 7/0012 |
| 2020/0043236 A1* | 2/2020 | Miller | G06T 19/006 |

FOREIGN PATENT DOCUMENTS

| | | |
|---|---|---|
| KR | 10-2013-0134680 A | 12/2013 |
| KR | 10-2016-0016717 A | 2/2016 |
| KR | 10-2016-0119400 A | 10/2016 |
| KR | 10-2017-0109962 A | 10/2017 |
| WO | WO 2015/057965 A1 | 4/2015 |

OTHER PUBLICATIONS

Ligaj et al., "A Convenient Photo-Based Approach for Assessing Body Posture", 2013 IEEE Internaional Conference on Multimedia and Expo (ICME), IEEE, Jul. 14, 2014, pp. 1-6, XP032639303.

Min et al., "Body Weight Analysis from Human Body Images", IEEE Transactions on Information Forensics and Security, IEEE, vol. 14, No. 10, Mar. 13, 2019, pp. 2676-2688.

* cited by examiner

BEAUTY COUNSELING INFORMATION PROVIDING DEVICE AND BEAUTY COUNSELING INFORMATION PROVIDING METHOD

CROSS-REFERENCE TO RELATED APPLICATION

This present application claims benefit of priority to Korean Patent Application No. 10-2019-0100132, entitled "BEAUTY COUNSELING INFORMATION PROVIDING DEVICE AND BEAUTY COUNSELING INFORMATION PROVIDING METHOD", filed on Aug. 16, 2019, in the Korean Intellectual Property Office, the entire disclosure of which is incorporated herein by reference.

BACKGROUND

1. Technical Field

The present disclosure relates to a beauty counseling information providing method and apparatus, and more particularly, to a beauty counseling information providing method and apparatus, which calculates a body feature by analyzing a set of images classified based on the purpose of providing counseling information from a plurality of pre-stored images, and provides beauty counseling information according to the body feature.

2. Description of Related Art

As life expectancy currently increases, diagnosis and management of a health condition is becoming more desirable. Obesity refers to the excessive accumulation of body fat in the body, which is caused by prolonged periods of energy imbalance in which the intake energy exceeds the consumed energy. It has been found that environmental factors such as a diet change and reduced activity due to westernization as well as genetic factors such as age, race, and family history are largely involved in obesity. The skin is an element of the human body facing the external environment, which contains various metabolic products and components, and sometimes becomes an indicator of the health condition.

The related art 1 discloses the content of measuring a body mass index (BMI) for diagnosing an obesity condition, and recommends exercise equipment for each user by monitoring a change in the body mass index.

The related art 2 discloses the content capable of diagnosing and managing a skin condition by mounting a portable spectroscopic imaging device on a user terminal such as a smartphone or a tablet.

As described above, the diagnosis of the obesity condition and the skin condition is performed through an electronic apparatus such as an obesity measuring apparatus or a skin diagnosis apparatus that directly contacts the user. However, the diagnosis method through the obesity measuring apparatus and the skin diagnosis apparatus has low accuracy and highly depends on the experience of the subject providing the diagnosis result. Meanwhile, the monitoring of the obesity and skin conditions for the diagnosis of the health condition needs to be performed continuously. Accordingly, there is a need for a method that may more easily perform monitoring and diagnosis even without causing discomfort to the user.

The above-described background art is technical information retained by the inventor to derive the present disclosure or acquired by the inventor while deriving the present disclosure, and thus should not be construed as art that was publicly known prior to the filing date of the present disclosure.

RELATED ART DOCUMENTS

Patent Documents

Related Art 1: Korean Patent Application Publication No. 10-2017-0109962 (published on Oct. 10, 2017)
Related Art 2: Korean Patent Application Publication No. 10-2016-0119400 (published on Oct. 13, 2016)

SUMMARY OF THE DISCLOSURE

An object of the present disclosure is to solve the problem of the related art in which it is difficult to continuously monitor by measuring the degree of obesity and a skin condition through an electronic apparatus, such as an obesity degree measuring apparatus, a skin diagnostic apparatus for the user.

Another object of the present disclosure is to solve the problem of the related art in which may cause discomfort to the user when measuring by measuring the degree of obesity and a skin condition through an electronic apparatus such as an obesity degree measuring apparatus, a skin diagnostic apparatus in a state contacting the user.

Still another object of the present disclosure is to calculate a body feature by analyzing the images captured and stored by the user, and to provide beauty counseling information to the user according to the body feature, thereby causing the user to be alert to physical health.

Yet another object of the present disclosure is to calculate the degree of obesity by analyzing the images captured and stored by the user, and to provide obesity related beauty counseling information to the user according to the degree of obesity, thereby causing the user to be alert to obesity.

Still yet another object of the present disclosure is to generate skin condition information by analyzing images captured and stored by the user, and to provide skin related counseling information to the user according to the skin condition, thereby causing the user to be alert to skin care.

A beauty counseling information providing method according to an embodiment of the present disclosure may include calculating a body feature by analyzing an image set classified based on the purpose of providing counseling information from a plurality of images previously stored, and providing beauty counseling information according to the body feature.

Specifically, the beauty counseling information providing method according to an embodiment of the present disclosure may include generating a first image set that has classified a plurality of images previously stored based on capturing information every predetermined period, generating a second image set that has classified a plurality of images included in the first image set based on the purpose of providing counseling information, calculating a body feature through comparative analysis of the plurality of images included in the second image set, and providing the beauty counseling information when the amount of change between the calculated body feature and previously stored existing body feature exceeds a predetermined value.

Through the beauty counseling information providing method according to the present embodiment, it is possible to calculate the body feature by analyzing images captured and stored by the user, and to provide the beauty counseling information to the user according to the body feature to cause the user to be alert to body health, thereby inducing body health care.

In addition, the generating the first image set may include generating the first image set that has classified the plurality of images stored every predetermined period based on a self-capturing mode in which a user directly captures himself or herself.

In addition, the generating the first image set may include generating the first image set that has classified the plurality of images stored every predetermined period into a plurality of images having the same capturing setting information including one or more among brightness, contrast, saturation, color, gamma, exposure, ISO sensitivity, aperture, and shutter speed.

In addition, the generating the first image set may include converting the plurality of images stored every predetermined period into a plurality of images having the same capturing setting information including one or more among brightness, contrast, saturation, color, gamma, exposure, ISO sensitivity, aperture, and shutter speed, and generating the plurality of images in which the capturing setting information has been identically converted as the first image set.

In addition, the generating the second image set may include generating the second image set that has classified the plurality of images included in the first image set into an image including a body part that is at least partially nude based on the purpose of providing counseling information on the degree of obesity.

In addition, the calculating the body feature may include separating an area including the body and an area not including the body from the plurality of images included in the second image set, and detecting an edge of the area including the body, and calculating a curvature of the edge.

In addition, the providing the beauty counseling information may include providing beauty counseling information including obesity related information, when the amount of change between the curvature and previously stored existing curvature exceeds a predetermined value.

In addition, the generating the second image set may include generating the second image set classified as the image including a face based on the purpose of providing counseling information on the degree of skin aging from the plurality of images included in the first image set.

In addition, the calculating the body feature may include detecting a facial area from the plurality of images included in the second image set, and generating skin condition information including one or more among shine, pores, wrinkles, fine wrinkles, pigmentation, skin redness, and sebum from the facial area.

In addition, the providing the beauty counseling information may include providing the beauty counseling information including skin aging related information, when the amount of change between the skin condition information and previously stored existing skin condition information exceeds a predetermined value.

A beauty counseling information providing apparatus according to an embodiment of the present disclosure may include a first generator for generating a first image set that has classified a plurality of images previously stored based on capturing information every predetermined period, a second generator for generating a second image set that has classified a plurality of images included in the first image set based on the purpose of providing counseling information, an analyzer for calculating a body feature through comparative analysis of the plurality of images included in the second image set, and a provider for providing beauty counseling information when the amount of change between the calculated body feature and previously stored existing body feature exceeds a predetermined value.

Through the beauty counseling information providing apparatus according to the present embodiment, it is possible to calculate the body feature by analyzing images captured and stored by the user, and to provide the beauty counseling information to the user according to the body feature to cause the user to be alert to body health, thereby inducing body health care.

In addition, the first generator may be configured to generate the first image set that has classified the plurality of images stored every predetermined period based on a self-capturing mode in which a user directly captures himself or herself.

In addition, the first generator may be configured to generate the first image set that has classified the plurality of images stored every predetermined period into a plurality of images having the same capturing setting information including one or more among brightness, contrast, saturation, color, gamma, exposure, ISO sensitivity, aperture, and shutter speed.

In addition, the first generator may be configured to convert the plurality of images stored every predetermined period into a plurality of images having the same capturing setting information including one or more among brightness, contrast, saturation, color, gamma, exposure, ISO sensitivity, aperture, and shutter speed, and generating the plurality of images in which the capturing setting information has been identically converted as the first image set.

In addition, the second generator may be configured to generate the second image set classified as the image including a face based on the purpose of providing counseling information on the degree of skin aging from the plurality of images included in the first image set.

In addition, the analyzer may be configured to separate an area including the body and an area not including the body from the plurality of images included in the second image set, and to detect an edge of the area including the body, and to calculate a curvature of the edge.

In addition, the provider may be configured to provide beauty counseling information including obesity related information, when the amount of change between the curvature and previously stored existing curvature exceeds a predetermined value.

In addition, the second generator may be configured to generate the second image set classified as the image including a face based on the purpose of providing counseling information on the degree of skin aging from the plurality of images included in the first image set.

In addition, the analyzer may be configured to detect a facial area from the plurality of images included in the second image set, and to generate skin condition information including one or more among shine, pores, wrinkles, fine wrinkles, pigmentation, skin redness, and sebum from the facial area.

In addition, the provider may be configured to provide the beauty counseling information including skin aging related information, when the amount of change between the skin condition information and previously stored existing skin condition information exceeds a predetermined value.

In addition, other methods and other systems for implementing the present disclosure, and a computer-readable medium for storing a computer program for executing the above method may be further provided.

Other aspects, features, and advantages will become apparent from the following drawings, claims, and detailed description of the disclosure.

According to the present disclosure, it is possible to monitor continuously by measuring the degree of obesity and the skin condition on the image captured by the user, thereby causing the user to lead a healthy life by inducing continuous obesity and skin care.

In addition, it is possible to measure the degree of obesity and the skin condition on the image captured by the user without the user having to contact the electronic apparatus such as the obesity degree measuring apparatus or the skin diagnosis apparatus, thereby solving the problem of the related art that may cause discomfort to the user when measuring.

In addition, it is possible to calculate the body feature by analyzing the images captured and stored by the user, and to provide the beauty counseling information to the user according to the body feature to cause the user to be alert to the physical health, thereby inducing the physical health care.

In addition, it is possible to calculate the degree of obesity by analyzing the images captured and stored by the user, and to provide the obesity related beauty counseling information to the user according to the degree of obesity to cause the user to be alert to obesity, thereby inducing the obesity care.

In addition, it is possible to calculate the skin condition information by analyzing the images captured and stored by the user, and to provide the skin aging related beauty counseling information to the user according to the skin condition to cause the user to be alert to the skin care, thereby inducing the skin care.

The effects of the present disclosure are not limited to those mentioned above, and other effects not mentioned may be clearly understood by those skilled in the art from the following description.

DETAILED DESCRIPTION OF THE EMBODIMENTS

Figure 1:
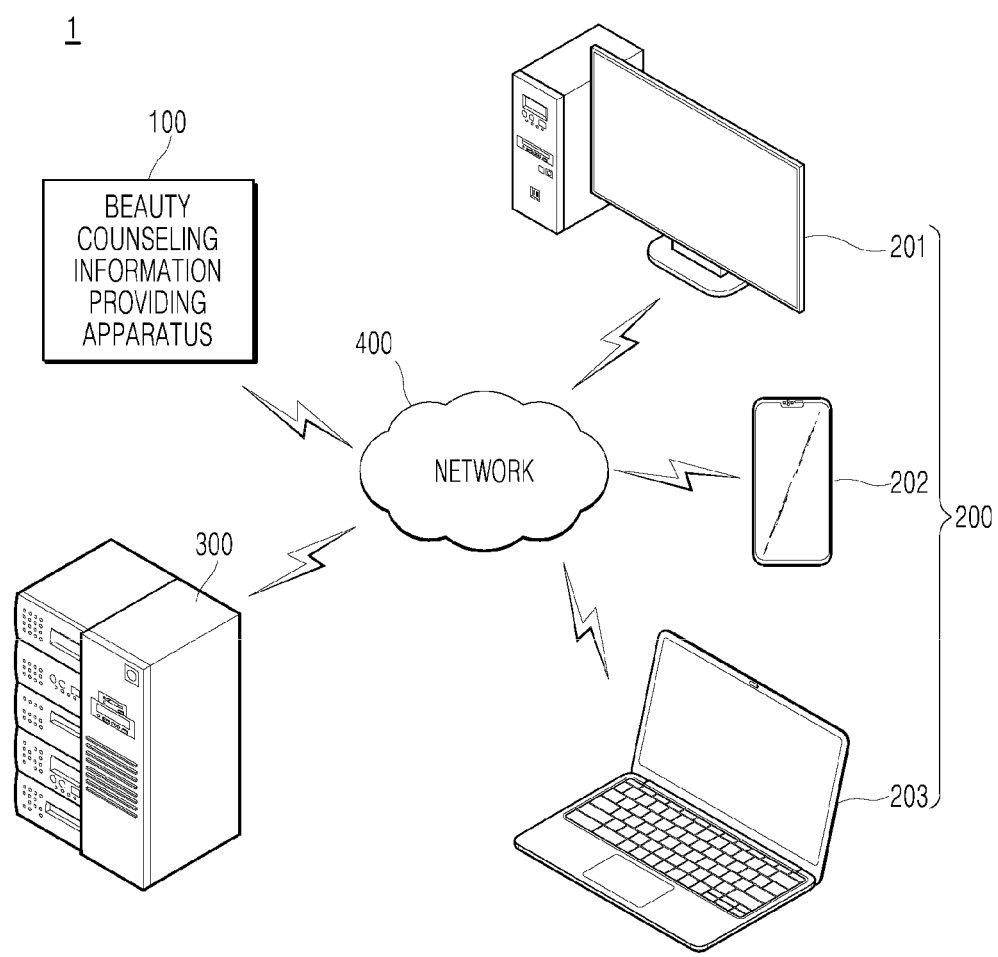
FIG. 1 is a diagram for schematically explaining a beauty counseling information providing system according to an embodiment of the present disclosure.

Advantages and features of the present disclosure and methods for achieving them will become apparent from the descriptions of aspects hereinbelow with reference to the accompanying drawings. However, the description of particular example embodiments is not intended to limit the present disclosure to the particular example embodiments disclosed herein, but on the contrary, it should be understood that the present disclosure is to cover all modifications, equivalents and alternatives falling within the spirit and scope of the present disclosure. The example embodiments disclosed below are provided so that the present disclosure will be thorough and complete, and also to provide a more complete understanding of the scope of the present disclosure to those of ordinary skill in the art. In the interest of clarity, not all details of the relevant art are described in detail in the present specification in so much as such details are not necessary to obtain a complete understanding of the present disclosure.

The terminology used herein is used for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "includes," "including," "containing," "has," "having" or other variations thereof are inclusive and therefore specify the presence of conditions, features, integers, steps, operations, elements, and/or components, but do not preclude the presence or addition of one or more other features, integers, steps, operations, elements, components, and/or groups thereof. Furthermore, these terms such as "first," "second," and other numerical terms, are used only to distinguish one element from another element. These terms are generally only used to distinguish one element from another.

Hereinafter, embodiments of the present disclosure will be described in detail with reference to the accompanying drawings. Like reference numerals designate like elements throughout the specification, and overlapping descriptions of the elements will not be provided.

FIG. 1 is a diagram for schematically explaining a beauty counseling information providing system according to an embodiment of the present disclosure. Referring to FIG. 1, a beauty counseling information providing system 1 may include a beauty counseling information providing apparatus 100, a user terminal 200, a server 300, and a network 400.

The beauty counseling information providing apparatus 100 may generate a first image set that has classified a plurality of images stored every predetermined period based on captured information.

Herein, the predetermined period may include a certain period including days to weeks. In addition, the predetermined period may include a time when the capturing event information for the user to start capturing is generated. Here, the time when the capturing event information is generated may include a time for receiving a shutter input signal input by the user from the user terminal 200. That is, whenever the capturing event information is generated, the beauty counseling information providing apparatus 100 may generate the first image set. If the capturing event information is successively generated plural times, the first image set may be generated by using the image after previous capturing event information has been generated to the image generated up to the time when the last capturing event information is generated.

In addition, the capturing information may include capturing mode information of the user terminal 200 when capturing an image, and for example, the capturing information may include a self-capturing mode, a continuous capturing mode, a moving picture capturing mode, etc. In addition, the capturing information may include capturing setting information as metadata stored together when the image is stored, and for example, the capturing setting information may include one or more among brightness, contrast, saturation, color, gamma, exposure, ISO sensitivity, aperture, and shutter speed of the captured image.

The beauty counseling information providing apparatus 100 may generate a second image set that has classified a plurality of images included in the first image set based on the purpose of providing counseling information. Here, the purpose of providing the counseling information may include one or more of the degree of obesity and the degree of skin aging, and one or more thereof may be set by the user.

In the case of the purpose of providing counseling information on the degree of obesity, the plurality of images included in the second image set may be images including body parts (a face, a chest, a waist, an arm, a leg, a hip, etc.) where at least some of the plurality of images included in the first image set are nude. For example, it may be seen that at least arms and legs of the user are nude in the image of the user in a swimsuit, and at least legs of the user are nude in the image of the user in shorts.

In addition, in the case of the purpose of providing the counseling information on the degree of skin aging, the plurality of images included in the second image set may include images including a face among the plurality of images included in the first image set.

The beauty counseling information providing apparatus 100 may calculate a body feature through comparative analysis of the plurality of images included in the second image set. Since the second image set may include the plurality of images, the value calculated as the average value after calculating the body feature for each image may be the body feature.

In the case of the purpose of providing the counseling information on the degree of obesity, the body feature may separate an area including the body and an area not including the body from the plurality of images included in the second image set, detect an edge of the area including the body, and include the result of calculating the curvature of the edge.

In the case of the purpose of providing the counseling information on the degree of skin aging, the body feature may detect a facial area from the plurality of images included in the second image set, and include the result of generating the skin condition information including one or more among shine, pores, wrinkles, fine wrinkles, pigmentation, skin redness, and sebum from the facial area.

The beauty counseling information providing apparatus 100 may provide beauty counseling information when the amount of change between the calculated body feature and the previously stored existing body feature exceeds a predetermined value.

Here, the beauty counseling information may include a value (for example, including that xx Kg fatter than in the past) on the degree of obesity, and a future body image compared to a current body image. Here, the future body image may include an image fatter than the current body image. For this purpose, the beauty counseling information providing apparatus 100 may use a previously trained deep neural network model to output the future body image predictive result by analyzing the body related information, thereby outputting the body image predictive result of the user at a specific future time by analyzing the body related information of the user including the body image of the user, the curvature calculation result, and the time information having captured the body image.

In addition, the beauty counseling information may include a value (for example, xx years older than in the past) of the degree of skin aging, and a future facial image compared to a current facial image. Here, the future facial image may include an image older than the current facial image. For this purpose, the beauty counseling information providing apparatus 100 may use a previously trained deep neural network model to output a future facial image predictive result by analyzing face related information, thereby outputting the facial image predictive result of the user at a specific future time by analyzing the face related information of the user including the facial image of the user, the result of generating the skin condition information, and the time information having captured the facial image.

As an optional embodiment, the beauty counseling information providing apparatus 100 may provide, as recommendation information, exercise information and/or diet information for resolving obesity when providing the counseling information on obesity. In addition, the beauty counseling information providing apparatus 100 may provide, as recommendation information, skin care information and/or diet information and/or procedure information that may alleviate skin aging when providing skin aging degree counseling information.

The user terminal 200 may receive a service for driving or controlling the beauty counseling information providing apparatus 100 through an authentication process after accessing a driving application of the beauty counseling information providing apparatus or a driving site of the beauty counseling information providing apparatus. In the present embodiment, the user terminal 200 that has completed the authentication process may drive the beauty counseling information providing apparatus 100, and control an operation of the beauty counseling information providing apparatus 100.

The user terminal 200 may include a communication terminal capable of executing a function of a computing device and executing a function of capturing images. In the present embodiment, the user terminal 200 may include, but is not limited to, a desktop computer 201, smartphone 202, notebook 203, tablet PC, smart TV, cell phone, personal digital assistant (PDA), laptop, media player, micro server, global positioning system (GPS) device, electronic book terminal, digital broadcast terminal, navigation device, kiosk, MP3 player, digital camera, home appliance, and other mobile or immobile computing devices operated by the user. Furthermore, the user terminal 200 may be a wearable terminal having a communication function and a data processing function, such as a watch, glasses, a hair band, or a ring. The user terminal 200 is not limited to the above-mentioned devices, and thus any terminal that supports web browsing may be adopted.

The server 300 may be a database server for providing the big data required for applying various artificial intelligence algorithm and data for operating the beauty counseling information providing apparatus 100. In addition, the server 300 may include a web server or an application server capable of controlling the operation of the beauty counseling information providing apparatus 100 by using the driving application of the beauty counseling information providing apparatus or the driving web browser of the beauty counseling information providing apparatus, which has been installed on the user terminal 200.

Here, the artificial intelligence (AI), which is an area of computer engineering and information technology for studying methods for enabling computers to mimic thinking, learning, self-development, or the like that may be carried out with human intelligence, may represent enabling computers to mimic human intelligent behavior.

In addition, artificial intelligence does not exist on its own, but is rather directly or indirectly related to a number of other fields in computer science. In recent years, there have been numerous attempts to introduce an element of AI into various fields of information technology to solve problems in the respective fields.

Machine learning is an area of artificial intelligence that includes the field of study that gives computers the capability to learn without being explicitly programmed. Specifically, the Machine Learning may be a technology for researching and constructing a system for learning, predicting, and improving its own performance based on empirical data and an algorithm for the same. Machine learning algorithms, rather than only executing rigidly-set static program commands, may be used to take an approach that builds models for deriving predictions and decisions from inputted data.

The server 300 may receive the plurality of images included in the second image set from the beauty counseling information providing apparatus 100, and calculate the body feature through comparative analysis of the plurality of images included in the second image set. The server 300 may generate beauty counseling information to transmit it to the beauty counseling information providing apparatus 100 when the amount of change between the calculated body feature and the previously stored existing body feature exceeds a predetermined value. The server 300 may generate and learn the deep neural network model in order to generate the beauty counseling information.

According to the processing capability of the beauty counseling information providing apparatus 100, at least some of the calculation of the body feature and the generation of the beauty counseling information may be performed by the beauty counseling information providing apparatus 100.

The network 400 may serve to connect the beauty counseling information providing apparatus 100, the user terminal 200, and the server 300. The network 400 may include, for example, wired networks such as local area networks (LANs), wide area networks (WANs), metropolitan area networks (MANs), and integrated service digital networks (ISDNs), or wireless networks such as wireless LANs, CDMA, Bluetooth, and satellite communication, but the scope of the present disclosure is not limited thereto. Furthermore, the network 400 may transmit and receive information using short-range communications or long-distance communications. Here, the short-range communications may include Bluetooth, radio frequency identification (RFID), infrared data association (IrDA), ultra-wideband (UWB), ZigBee, and wireless fidelity (Wi-Fi) technology.

The long-distance communications may include code division multiple access (CDMA), frequency division multiple access (FDMA), time division multiple access (TDMA), orthogonal frequency division multiple access (OFDMA), and single carrier frequency division multiple access (SC-FDMA) technology.

The network 400 may include a connection of network elements such as a hub, a bridge, a router, a switch, and a gateway. The network 400 may include one or more connected networks, including a public network such as the Internet and a private network such as a secure corporate private network. For example, the network may include a multi-network environment. The access to the network 400 may be provided via one or more wired or wireless access networks. Furthermore, the network 400 may support the Internet of things (IoT) for 5G communication or exchanging and processing information between distributed elements such as objects.

Figure 2:
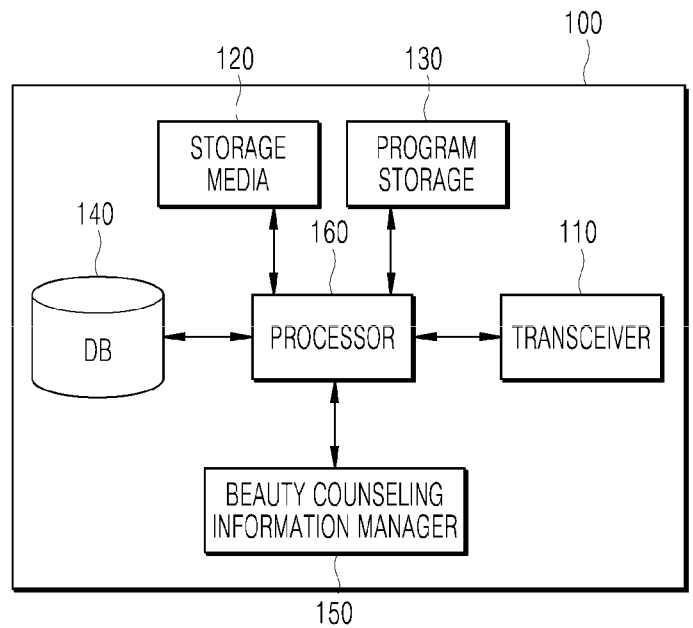
FIG. 2 is a diagram for schematically explaining a detailed configuration of a beauty counseling information providing apparatus of the beauty counseling information providing system of FIG. 1.

FIG. 2 is a diagram for schematically explaining a detailed configuration of a beauty counseling information providing apparatus in the beauty counseling information providing system of FIG. 1. Hereinbelow, the common parts previously described with reference to FIG. 1 will not be described, to avoid repetitive description. Referring to FIG. 2, the beauty counseling information providing apparatus 100 may include a transceiver 110, a storage media 120, a program storage 130, a database 140, a beauty counseling information manager 150, and a controller 160.

The transceiver 110 interlocks with the network 400 to provide a communication interface required for providing a transmission/reception signal between the beauty counseling information providing apparatus 100 and/or the user terminal 200 and/or the server 300 in the form of packet data. Furthermore, the transceiver 110 may serve to receive a predetermined information request signal from the user terminal 200, and serve to transmit the information processed by the beauty counseling information providing apparatus 100 to the electronic user terminal 200. Furthermore, the transceiver 110 may transmit the predetermined information request signal from the user terminal 200 to the server 300, may receive a response signal processed by the server 300, and may transmit the response signal to the user terminal 200. Furthermore, the transceiver 110 may be a device including hardware and software required for transmitting and receiving signals such as a control signal and a data signals via a wired or wireless connection to another network device.

Furthermore, the transceiver 110 may support a variety of object-to-object intelligent communication, for example, Internet of things (IoT), Internet of everything (IoE), and Internet of small things (IoST), and may support, for example, machine to machine (M2M) communication, vehicle to everything (V2X) communication, and device to device (D2D) communication.

In the present embodiment, the storage media 120 may temporarily or permanently store data processed by the controller 160. In addition, the storage media 120 may store various information required for the operation of the beauty counseling information providing apparatus 100, and include a volatile or nonvolatile recording medium. In addition, the storage media 120 may store a plurality of images captured by the user.

Here, the storage media 120 may include magnetic storage media or flash storage media, but the present disclosure is not limited thereto. This memory 120 may include an internal memory and an external memory, and may include: a volatile memory such as a DRAM, SRAM, or SDRAM; a non-volatile memory such as a one-time programmable ROM (OTPROM), PROM, EPROM, EEPROM, mask ROM, flash ROM, NAND flash memory, or NOR flash memory; and a storage device such as an HDD or a flash drive such as an SSD, compact flash (CF) card, SD card, micro-SD card, mini-SD card, Xd card, or a memory stick.

The program storage 130 may mount a control software for performing a task for generating the first image set that has classified the plurality of images stored every predetermined period based on the capturing information, a task for generating the second image set that has classified the plurality of images included in the first image set based on the purpose of providing counseling information, a task for calculating the body feature through the comparative analysis of the plurality of images included in the second image set, a task for providing the beauty counseling information when the amount of change between the calculated body feature and the previously stored existing body feature exceeds a predetermined value, a task for providing, as recommendation information, exercise information and/or diet information capable of resolving obesity when providing the counseling information on the degree of obesity among the beauty counseling information, a task for providing, as recommendation information, skin care information and/or diet information and/or procedure information capable of alleviating skin aging when providing the skin aging degree counseling information among the beauty counseling information, etc.

The database 140 may include a management database for storing the information collected and generated by the beauty counseling information providing apparatus 100. Here, the management database may store the recommendation information including the first image set generation information, the second image set generation information, the existing body feature information, the existing skin condition information, the calculated body curvature information, the generated face skin condition information, the time information generating the beauty counseling information, the recommendation information including the exercise information and the diet information capable of resolving obesity, and the recommendation information including the skin care information, the diet information, and the procedure information capable of alleviating skin aging.

Furthermore, the database 140 may further include a user database for storing basic information related to the user. Here, the user database may store user information on the user who wants to receive the beauty counseling information. Here, the user information may include: basic information on a user, such as name, affiliation, personal data, gender, age, contact information, email, and address; authentication (login) information such as an ID (or email) and a password; and access-related information such as an access country, an access location, information about a device used for access, and an accessed network environment. In addition, the user database may include information on the amount of change in the accumulated curvature of the body for each user, information on the amount of change in the accumulated skin condition of the face, information on the amount of change in the calculated curvature of the body, information on the amount of change in the generated skin condition of the face, and time information for generating the beauty counseling information.

The beauty counseling information manager 150 may generate the first image set that has classified the plurality of images stored every predetermined period based on capturing information, generate the second image set that has classified the plurality of images included in the first image set based on the purpose of providing the counseling information, calculate the body feature through the comparative analysis of the plurality of images included in the second image set, and provide the beauty counseling information when the amount of change between the calculated body feature and the previously stored existing body feature exceeds a predetermined value.

In the present embodiment, the beauty counseling information manager 150 may perform learning in connection with the controller 160 or receive a leaning result from the controller 160. In the present embodiment, the beauty counseling information manager 150 may also be provided outside the controller 160 as shown in FIG. 2, also provided inside the controller 160 to operate like the controller 160, and also provided inside the server 300 of FIG. 1. Hereinafter, a detailed description of the beauty counseling information manager 150 will be described with reference to FIG. 3.

The controller 160 may control the overall operation of the beauty counseling information providing apparatus 100 by driving the control software mounted in the program storage 130 as a kind of a central processing unit. The controller 160 may include any type of device capable of processing data, such as a processor. Here, the term "processor" may represent, for example, a hardware-embedded data processing device having a physically structured circuit to execute functions expressed as instructions or codes included in a program. Examples of the hardware-embedded data processing device may include a microprocessor, a central processing unit (CPU), a processor core, a multiprocessor, an application-specific integrated circuit (ASIC), and a field programmable gate array (FPGA), but the scope of the present disclosure is not limited thereto.

In the present embodiment, the controller 160 may perform machine learning such as deep learning on an image collected during a predetermined period so that the beauty counseling information providing apparatus 100 provides optimal beauty counseling information, and the storage media 120 may store data used for machine learning, result data, etc.

Deep learning, which is a subfield of machine learning, enables data-based learning through multiple layers. As the number of layers in deep learning increases, the deep learning network may acquire a collection of machine learning algorithms that extract core data from multiple datasets.

Deep learning structures may include an artificial neural network (ANN), and may include a convolutional neural network (CNN), a recurrent neural network (RNN), a deep belief network (DBN), and the like. The deep learning structure according to the present embodiment may use various structures well known in the art. For example, the deep learning structure according to the present disclosure may include a CNN, an RNN, a DBN, and the like. RNN is an artificial neural network structure which is formed by building up layers at each instance, and which is heavily used in natural language processing and the like and effective for processing time-series data which vary over a course of time. A DBN includes a deep learning structure formed by stacking up multiple layers of a deep learning scheme, restricted Boltzmann machines (RBM). A DBN has the number of layers formed by repeating RBM training. A CNN includes a model mimicking a human brain function, built under the assumption that when a person recognizes an object, the brain extracts the most basic features of the object and recognizes the object based on the results of complex processing in the brain.

Further, the artificial neural network may be trained by adjusting weights of connections between nodes (if necessary, adjusting bias values as well) to produce a desired output from a given input. Also, the artificial neural network may continuously update the weight values through learning. Furthermore, methods such as back propagation may be used in training the artificial neural network.

Meanwhile, the controller 160 may be mounted with an artificial neural network, and may perform the calculation of the body feature based on machine learning and the generation of the beauty counseling information by using the collected image of the user as an input data.

The controller 160 may include an artificial neural network, for example, a deep neural network (DNN) such as a CNN, an RNN, or a DBN, and may learn a deep neural network. Machine learning paradigms, in which the ANN operates, may include unsupervised learning and supervised learning. The controller 160 may control to update an artificial neural network structure after learning according to a setting.

Figure 3:
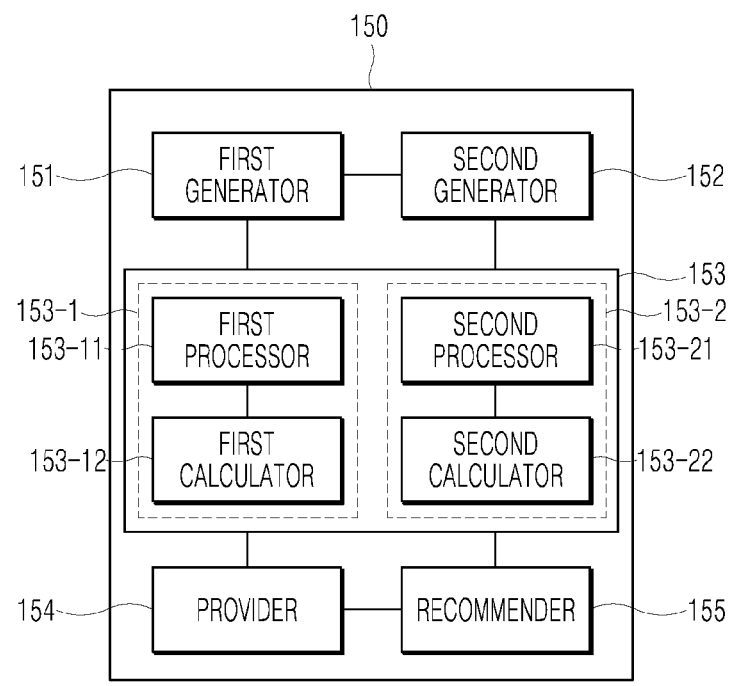
FIG. 3 is a diagram for schematically explaining a detailed configuration of a beauty counseling information manager of the beauty counseling information providing apparatus of FIG. 2.

FIG. 3 is a diagram for schematically explaining a detailed configuration of the beauty counseling information manager of the beauty counseling information providing apparatus of FIG. 2. In the following description, portions duplicative of the description of FIGS. 1 and 2 will be omitted. Referring to FIG. 3, the beauty counseling information manager 150 may include a first generator 151, a second generator 152, an analyzer 153, a provider 154, and a recommender 155.

The first generator 151 may generate the first image set that has classified the plurality of images stored in the storage media 120 based on capturing information every predetermined period. Here, the capturing information may include capturing mode information set by the user before capturing the image, and for example, may include a self-capturing mode, a continuous capturing mode, a moving picture capturing mode, etc. In addition, the capturing information may include capturing setting information as metadata stored together when the image is stored after capturing the image, and for example, the capturing setting information may include one or more among the brightness, contrast, saturation, color, gamma, exposure, ISO sensitivity, aperture, and shutter speed of the captured image.

The first generator 151 may generate the first image set that has classified the plurality of images stored in the storage media 120 every predetermined period based on a self-capturing mode in which the user directly captures himself or herself. That is, the first generator 151 may generate, as the first image set, images captured in a self-capturing mode in which the user directly captures himself or herself among the plurality of images. The images captured in the self-capturing mode may have similar capturing composition, capturing distance, and capturing setting information, thereby improving reliability of the body feature calculation.

In addition, the first generator 151 may generate the first image set that has classified the plurality of images stored in the storage media 120 into the plurality of images having the same capturing setting information including one or more among brightness, contrast, saturation, color, gamma, exposure, ISO sensitivity, aperture, and shutter speed, every predetermined period. That is, the first generator 151 may generate the images having the same capturing setting information among the plurality of images as the first image set.

In addition, the first generator 151 may convert the plurality of images stored in the storage media 120 into the plurality of images having the same capturing setting information including one or more among brightness, contrast, saturation, color, gamma, exposure, ISO sensitivity, aperture, and shutter speed, and generate the plurality of images that the capturing setting information has been identically converted as the first image set, every predetermined period.

The plurality of images stored in the storage media 120 may have the same capturing setting information or different capturing setting information. When the capturing setting information is different, the reliability may be reduced when calculating the body feature on the image in order to provide the beauty counseling information. Accordingly, the first generator 151 may convert the plurality of images having different capturing setting information into the plurality of images having the same capturing setting information, and generate the plurality of images having the same capturing setting information as the first image set, every predetermined period. For this purpose, the first generator 151 may further include an image processor capable of changing the capturing setting information. The image processor may convert and process each image so that one or more of brightness, contrast, saturation, color, gamma, exposure, ISO sensitivity, aperture, and shutter speed are the same.

As an optional embodiment, the image processor may reduce noise on the image stored in the storage media 120, and perform gamma correction, color filter array interpolation, color matrix, color correction, color enhancement, etc. Further, the image processor may perform functions such as a coloring process, a blurring process, an edge emphasizing process, an image analysis process, an image recognition, and an image effect process. Facial recognition, scene recognition, and the like may be performed for the image recognition. For example, brightness level adjustment, color correction, contrast adjustment, contour enhancement adjustment, screen division processing, character image generation, and image synthesis processing may be performed. The image processor may be provided in the camera of the user terminal 200, provided in the first generator 151, provided in the analyzer 153, provided in the controller 160, or provided as a separate device.

The second generator 152 may generate the second image set that has classified the plurality of images included in the first image set based on the purpose of providing the counseling information. That is, the second generator 152 may generate different second image sets according to the purpose of providing the counseling information. Here, the purpose of providing the counseling information may include one or more of the degree of obesity and the degree of skin aging.

In the case of the purpose of providing the counseling information on the degree of obesity, the second generator 152 may generate the second image set that has classified the plurality of images included in the first image set into the plurality of images including a body part that is at least partially nude. Here, the body may include a face, a neck, a shoulder, a chest, a waist, a hip, an arm, a leg, etc., and the second generator 152 may include the image including the a body part that is at least partially nude from the plurality of images included in the first image set in the second image set.

In the case of the purpose of providing the counseling information on the degree of skin aging, the second generator 152 may generate the second image set that has classified the plurality of images included in the first image set into the plurality of images including a face. That is, the second generator 152 may include the image including a face from the plurality of images included in the first image set in the second image set.

The analyzer 153 may calculate a body feature through comparative analysis of the plurality of images included in the second image set. In the present embodiment, the analyzer 153 may include a first analyzer 153-1 and a second analyzer 153-2 according to the purpose of providing the counseling information.

In the case of the purpose of providing the counseling information on the degree of obesity, the first analyzer 153-1 may calculate the amount of change in the curvature for the body through comparative analysis of the plurality of images included in the second image set. In the present embodiment, the first analyzer 153-1 may include a first processor 153-11 and a first calculator 153-12.

The first processor 153-11 may separate an area including the body and an area not including the body from the plurality of images included in the second image set. Here, the area including the body may correspond to the foreground area in the image, and the area not including the body may correspond to the background area in the image. The first processor 153-11 may apply a Gaussian model to the image to determine whether it is the pixel of the foreground image or the pixel of the background image, thereby separating the area including the body and the area not including the body from the image.

The first processor 153-11 may detect the edge of the area including the body. Here, the detection of the edge (contour) basically shows a contour at the boundary between two areas having different contrast, and may detect a portion where the brightness of the pixel changes larger than a threshold by operation. As the operation used for detecting the edge, a laplacian operation method or a canny operation method may be applied. Since the laplacian operation method uses the second derivative and shows the feature that recognizes only the points, which are locally the maximum, as a contour, only the contour existing at the center of the contour may be displayed, thereby showing the locality of the contour well. In the canny operation method, a noise removing mask is used before detecting the contour, and various types of contour detection masks may be used, such that only strong contours may be efficiently detected.

In order to calculate the curvature of the edge (contour), the first calculator 153-12 may extract the line forming a curvature with the center point of the curvature used for determining the curvature, and calculate the curvature by using the length (radius) and the angle from the center point of the curvature to the line forming the curvature.

Here, the first calculator 153-12 may calculate different curvatures according to the body parts, and apply different weights when calculating the curvatures according to the body parts. For example, if the body parts in the 10 images included in the second image set include 10 faces, 3 chests, and 1 leg, the highest weight may be applied when calculating the curvature of the face, and the lowest weight may be applied when calculating the curvature of the leg. That is, different weights may be applied according to the frequency of exposure of the body parts shown in the image. Later, the provider 154 may provide counseling information on the degree of obesity in response to the curvature calculated by the first calculator 153-12, and provide the value of the degree of obesity for each body part with respect to the full body image of the user, such that the user may confirm its overall change.

In the case of the purpose of providing the counseling information on the degree of skin aging, the second analyzer 153-2 may generate skin condition information on the face through comparative analysis of the plurality of images included in the second image set. In the present embodiment, the second analyzer 153-2 may include a second processor 153-21 and a second calculator 153-22.

The second processor 153-21 may detect a facial area from the plurality of images included in the second image set. The second processor 153-21 may remove the background area from the plurality of images included in the second image set, detect a specific component (eyes, a nose, a mouth, etc.) in the face, and detect a specific component based on the specific component in the facial area. The second processor 153-21 may extract face information including the facial area from the image by using an Adaboost algorithm, which is a representative face detection algorithm.

The second processor 153-21 may generate skin condition information including one or more among shine, pores, wrinkles, fine wrinkles, pigmentation, skin redness, and sebum from the facial area.

The second processor 153-21 may recognize the shine area in comparison with the surrounding gray value by using a cross mask method on the facial area image, and the recognized shine area may be selected as the upper 2% brightness pixel value. The shine area selected as the upper 2% brightness pixel value may be included in the skin condition information of the user.

The second processor 153-21 may generate skin condition information of the user including the pores by using the facial area image. Since the pores are relatively dark compared to the surroundings and have a round shape, the second processor 153-21 may first detect a dark area from the facial area image, and separately detect and remove similar dark hairs. The second processor 153-21 may use a morphology technique in order to separate the pores having smaller size or loosely connected and detected, and since the value of the pores is important in size and depth, the second processor 153-21 may calculate the value of the pores by multiplying the size and depth for every pixel and dividing it by a value of the size of the facial area image.

The second processor 153-21 may generate skin condition information of the user including wrinkles and fine wrinkles by using the facial area image. Since the wrinkles and the fine wrinkles are also shown relatively compared to the surroundings like pores, the second processor 153-21 may first detect a dark area from the facial area image, and separately detect and remove similar dark hairs. Since the important factor in wrinkles is length and depth, the second processor 153-21 may regard the area having the length equal to or smaller than a certain value or having a lighter depth than the average as fine wrinkles. The second processor 153-21 may calculate the length and depth of the wrinkles by using the S (saturation) channel of the hue-lightness-saturation (HLS) color model having a value similar to an actual depth with respect to the depth of the wrinkles, multiplying the length and average depth values in each area finally determined as wrinkles, and dividing it by the value of the size of the facial area image.

The second processor 153-21 may generate skin condition information of the user including pigmentation by using the facial area image. The second processor 153-21 leaves only the melanin pigment when detecting the dark pigmented area with the brightness value of the facial area image, and then removing the red pigment by using the color difference value. Before that, the hair is detected and removed. The pigment is calculated only by its brightness values, and the pigmentation may be calculated by firstly applying a weight thereto according to its darkness and secondly applying a weight to the darkness relative to its surroundings and then summing them and dividing it by the value of the size of the facial area image.

The second processor 153-21 may generate skin condition information of the user including skin redness by using the facial area image. Since the R (red) and G (green) color channels of the facial area image are different from the surroundings, the second processor 153-21 may calculate the skin redness by calculating it by a combination of the difference between the R color channel and the G color channel and a constant value and then dividing it by the value of the size of the facial area image.

The second processor 153-21 may generate skin condition information of the user including sebum by using the facial area image. The facial area image has porphyrin that looks red and clogged pores that look halfway between yellow and green. The two may be separately analyzed, but it is called sebum and the second processor 153-21 may show the porphyrin and the clogged pores detected from the facial area image and calculate it by the percentage relative to the size of the facial area image.

The second processor 153-21 may generate condition information of the object including the skin tone by using the facial area image. The second processor 153-21 may generate the skin condition information of the user including the skin tone on the facial area image by converting RGB data of the facial area image into CIE LAB color data, mapping the CIE LAB color data to color chart data, and matching the color chart data to a Fitzpatrick classification grade or color chart data.

The second calculator 153-22 may calculate a numerical value for the skin condition information generated by the second processor 153-21. For example, the second calculator 153-22 may calculate the size of the pores as a numerical value, and calculate the length and depth of the wrinkles as a numerical value.

The provider 154 may provide beauty counseling information when the amount of change between the calculated body feature and previously stored existing body feature exceeds a predetermined value (for example, 10%). The provider 154 may provide counseling information on the degree of obesity when the amount of change between the calculated curvature and previously stored existing curvature exceeds a predetermined value, and provide counseling information on the degree of aging when the amount of change between the generated skin condition information and previously stored existing skin condition information exceeds a predetermined value.

In the case of the purpose of providing the counseling information on the degree of obesity, the provider 154 may provide a value of the degree of obesity (for example, including that it has been xx kg fatter than the past), and a warning text together with a future body image relative to a current body image. Here, the future body image may include an image fatter than the current body image.

In the case of the purpose of providing the counseling information on the degree of skin aging, the provider 154 may provide a value of the degree of skin aging (for example, including that it has been xx years older than the past), and a warning text together with a future facial image relative to a current facial image. Here, the future facial image may include an image older than the current facial image.

The recommender 155 may provide, as recommendation information, exercise information and/or diet information for resolving obesity when providing the degree of obesity counseling. In addition, the recommender 155 may provide, as recommendation information, skin care information and/or diet information and/or procedure information that may alleviate skin aging when providing skin aging degree counseling information.

Figure 4:
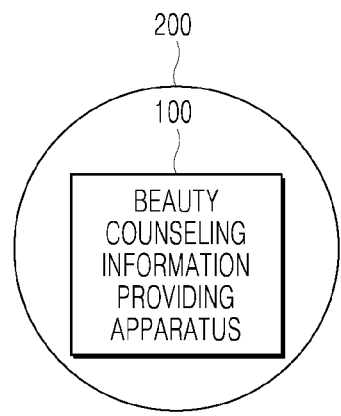
FIG. 4 is a diagram for schematically explaining a beauty counseling information providing system according to another embodiment of the present disclosure.

FIG. 4 is a diagram for schematically explaining a beauty counseling information providing system according to another embodiment of the present disclosure. In the following description, a description of portions duplicative of the description of FIGS. 1 to 3 will be omitted.

Referring to FIG. 4, the beauty counseling information providing apparatus 100 may be included in the user terminal 200. There are various methods that include the beauty counseling information providing apparatus 100 in the user terminal 200. As a specific embodiment, the beauty counseling information providing apparatus 100 may be installed in the user terminal 200 through the network 400, and for example, the beauty counseling information providing apparatus 100 may be installed in the user terminal 200 as one application form. As another specific embodiment, the beauty counseling information providing apparatus 100 may also be installed in the user terminal 200 through offline. However, this is an exemplary form and the present disclosure is not limited thereto, and may include a case where the beauty counseling information providing apparatus 100 may be installed in the user terminal 200 in various forms.

Figure 5:
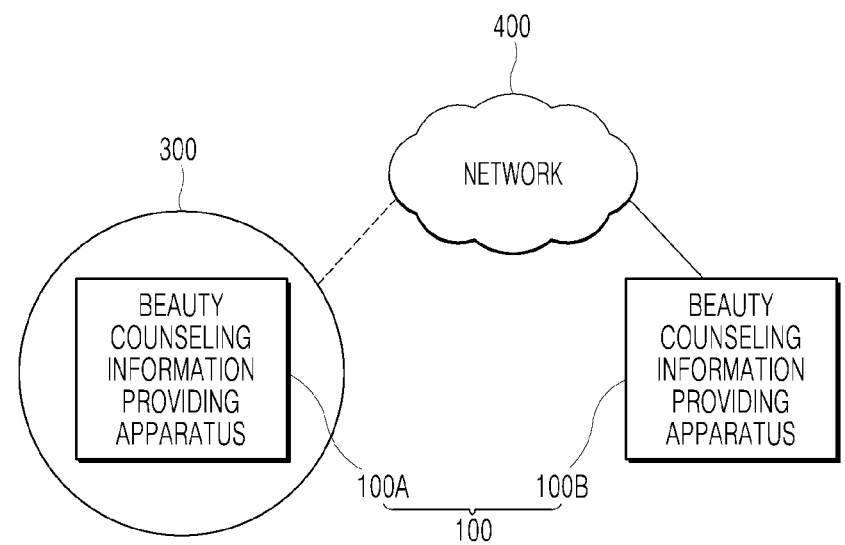
FIG. 5 is a diagram for schematically explaining a beauty counseling information providing system according to still another embodiment of the present disclosure.

FIG. 5 is a diagram for schematically explaining a beauty counseling information providing system according to still another embodiment of the present disclosure. In the following description, a description of the portions duplicative of the description of FIGS. 1 to 4 will be omitted.

Referring to FIG. 5, a part 100A of the beauty counseling information providing apparatus 100 may be included in the server 300, and the other part 100B may be connected with the server 300 through the network 400.

For example, the part 100A including the analyzer 153 and the provider 154 among the members of the beauty counseling information providing apparatus 100 shown in FIGS. 1 to 3 may be included in the server 300. Since the method for allowing the part 100A of the beauty counseling information providing apparatus 100 to be included in the server 300 is as described in an embodiment of FIG. 4, a detailed description thereof will be omitted. In addition, the other part 100B including the first generator 151, the second generator 152, and the recommender 155 among the members of the beauty counseling information providing apparatus 100 shown in FIGS. 1 to 3 may be connected with the server 300 through the network 400.

In the present embodiment, although the case where the first generator 151, the second generator 152, and the recommender 155 among the members of the beauty counseling information providing apparatus 100 are connected with the server 300 through the network 400 as the part 100B has been described, this is an embodiment and the present disclosure is not limited thereto. That is, at least any one among the plurality of members included in the beauty counseling information providing apparatus 100 may be selectively connected with the server 300 by the network 400.

Figure 6:
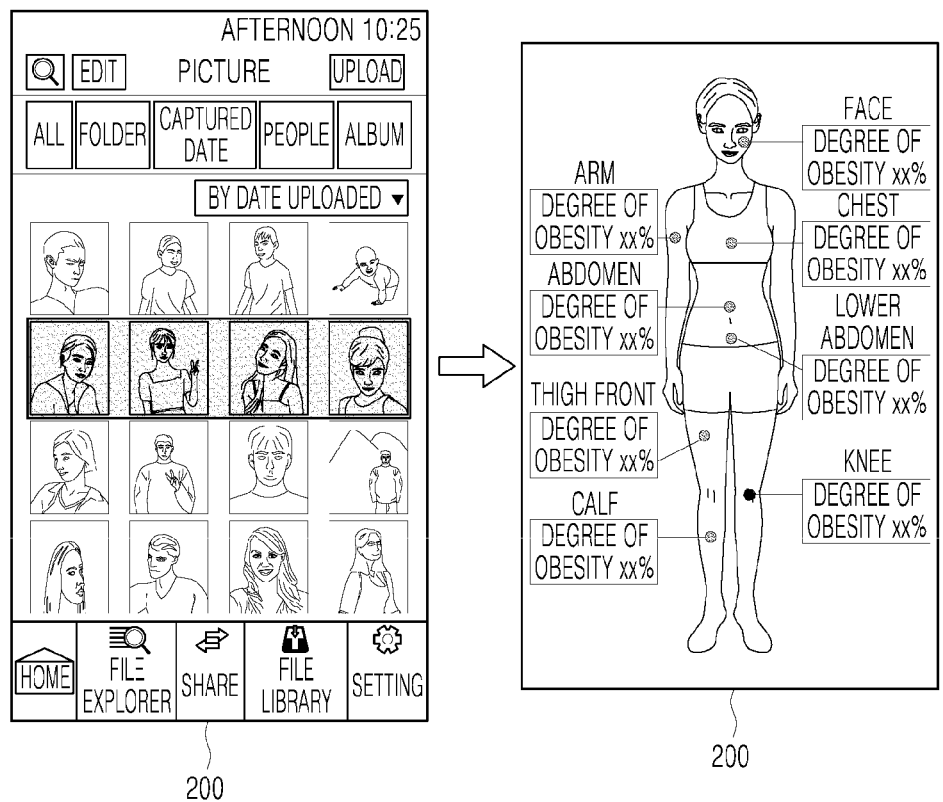
FIG. 6 is an exemplary diagram of beauty counseling information provided by the beauty counseling information providing apparatus according to an embodiment of the present disclosure.

FIG. 6 is an exemplary diagram of the beauty counseling information provided by the beauty counseling information providing apparatus according to an embodiment of the present disclosure. In the following description, a description of the portions duplicative of the description of FIGS. 1 to 5 will be omitted.

Referring to FIG. 6, shown is the situation where the beauty counseling information providing apparatus 100 is included in the user terminal 200, and the beauty counseling information providing apparatus 100 calculates the curvature of the body from the images included in the second image set among the plurality of images stored in the user terminal 200, and provides the beauty counseling information including obesity related information by the amount of change between the calculated curvature and previously stored existing curvature exceeding a predetermined value. In FIG. 6, the user may confirm its overall change by providing a value of the degree of obesity for each body part with respect to the full body image of the user.

Figure 7:
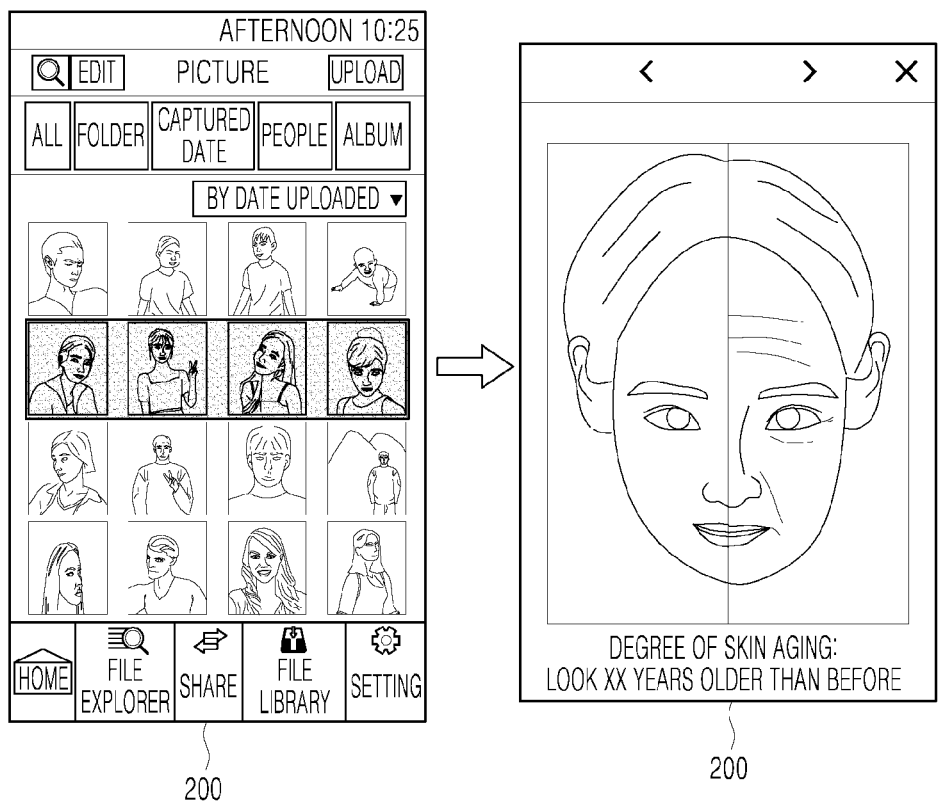
FIG. 7 is an exemplary diagram of beauty counseling information provided by the beauty counseling information providing apparatus according to another embodiment of the present disclosure.

FIG. 7 is an exemplary diagram of the beauty counseling information provided by the beauty counseling information providing apparatus according to yet another embodiment of the present disclosure. In the following description, a description of the portions duplicative of the description of FIGS. 1 to 6 will be omitted.

Referring to FIG. 7, shown is the situation where the beauty counseling information providing apparatus 100 is included in the user terminal 200, and the beauty counseling information providing apparatus 100 generates the skin condition information of the face from the images included in the second image set among the plurality of images stored in the user terminal 200, and providing the beauty counseling information including skin aging related information by the amount of change between the generated skin condition information of the face and previously stored existing skin condition information exceeding a predetermined value. In FIG. 7, the user may intuitively confirm its skin condition change by providing the current skin condition and the future skin condition with respect to the facial image of the user.

Figure 8:
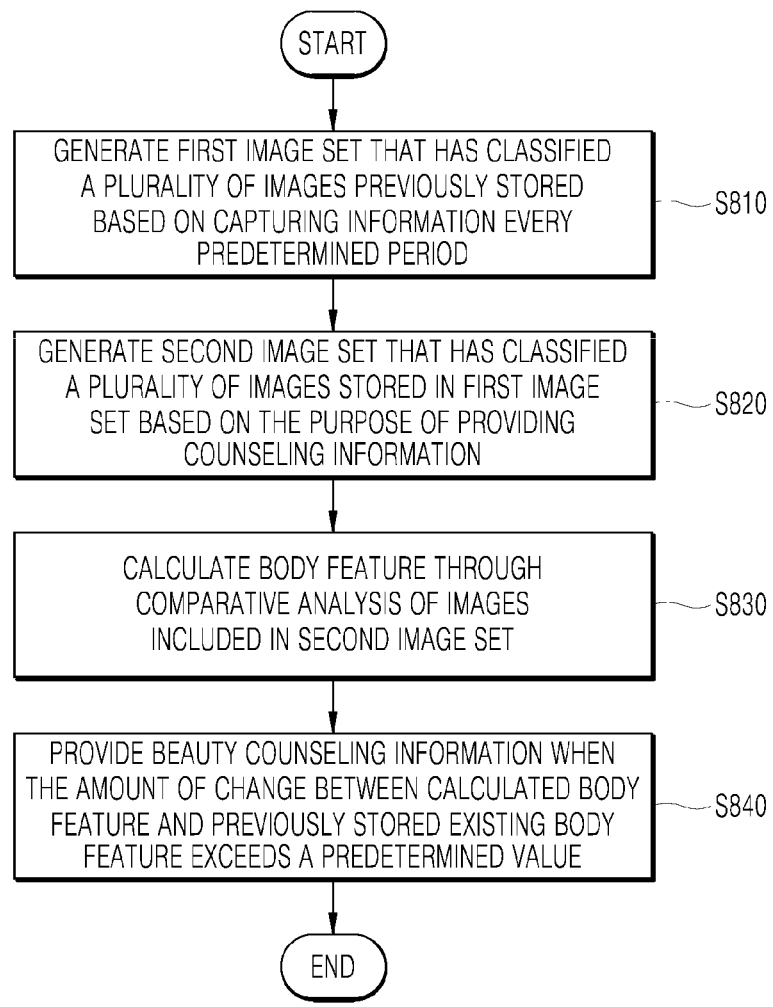
FIG. 8 is a flowchart for explaining a beauty counseling information providing method according to an embodiment of the present disclosure.

FIG. 8 is a flowchart for explaining a beauty counseling information providing method according to an embodiment of the present disclosure. In the following description, a description of the portions duplicative of the description of FIGS. 1 to 7 will be omitted.

Referring to FIG. 8, in operation S810, the beauty counseling information providing apparatus 100 generates a first image set that has classified a plurality of images stored based on capturing information every predetermined period. Here, the capturing information may include capturing mode information of the user terminal 200 when capturing an image, and may include, for example, a self-capturing mode, a continuous capturing mode, a moving picture capturing mode, etc. In addition, the capturing information may include capturing setting information as metadata stored together when the image is stored, and for example, the capturing setting information may include one or more among brightness, contrast, saturation, color, gamma, exposure, ISO sensitivity, aperture, and shutter speed of the captured image.

In operation 5820, the beauty counseling information providing apparatus 100 generates a second image set that has classified a plurality of images included in the first image set based on the purpose of providing counseling information. Here, the purpose of providing the counseling information may include one or more of the degree of obesity and the degree of skin aging, and at least one thereof may be set by the user's selection. In the case of the purpose of providing the counseling information on the degree of obesity, the beauty counseling information providing apparatus 100 may include an image including a body part that is at least partially nude from the plurality of images included in the first image set in the second image set. In addition, in the case of the purpose of providing the counseling information on the degree of skin aging, the beauty counseling information providing apparatus 100 may include an image including a face from the plurality of images included in the first image set in the second image set.

In operation S830, the beauty counseling information providing apparatus 100 calculates a body feature through comparative analysis of the plurality of images included in the second image set. In the case of the purpose of providing the counseling information on the degree of obesity, the body feature may separate an area including the body and an area not including the body from the plurality of images included in the second image set, detect the edge of the area including the body, and include the result of calculating the curvature of the edge. In the case of the purpose of providing the counseling information on the degree of skin aging, the body feature may detect a facial area from the plurality of images included in the second image set, and include the result of generating the skin condition information including one or more among shine, pores, wrinkles, fine wrinkles, pigmentation, skin redness, and sebum from the facial areas.

In operation S840, the beauty counseling information providing apparatus 100 provides beauty counseling information when the calculated body feature exceeds a predetermined ratio. The beauty counseling information providing apparatus 100 may provide beauty counseling information including obesity related information when the amount of change between the calculated curvature and the previously stored existing curvature exceeds a predetermined value, and provide counseling information on the degree of aging when the amount of change between the generated skin condition information and the previously stored existing skin condition information exceeds a predetermined value. In the case of the purpose of providing the counseling information on the degree of obesity, the beauty counseling information providing apparatus 100 may provide a value of the degree of obesity (for example, including that it has been xx Kg fatter than the past), and a warning text together with a future body image relative to a current body image. In the case of the purpose of providing the counseling information on the degree of skin aging, the beauty counseling information providing apparatus 100 may provide a value of the degree of skin aging (for example, including that it has been xx years older than the past), and a warning text together with a future facial image relative to a current facial image.

As an optional embodiment, the beauty counseling information providing apparatus 100 may provide, as recommended information, exercise information and/or diet information for resolving obesity when providing the obesity degree counseling information. In addition, the beauty counseling information providing apparatus 100 may provide, as recommendation information, skin care information and/or diet information and/or procedure information that may alleviate skin aging when providing the skin aging degree counseling information.

The embodiments of the present disclosure described above may be implemented through computer programs executable through various components on a computer, and such computer programs may be recorded in computer-readable media. Examples of the computer readable medium may include magnetic media such as a hard disk drives (HDD), floppy disks and a magnetic tapes, optical media such as CD-ROMs and DVDs, magneto-optical media such as floptical disks, or hardware devices such as ROMs, RAMs, and flash memories specifically configured to store and execute program commands.

Meanwhile, the computer programs may be those specially designed and constructed for the purposes of the present disclosure or they may be of the kind well known and available to those skilled in the computer software arts. Examples of program code include both a machine code, such as produced by a compiler, and a higher-level code that may be executed by the computer using an interpreter.

As used in the present application (especially in the appended claims), the terms "a/an" and "the" include both singular and plural references, unless the context clearly conditions otherwise. Also, it should be understood that any numerical range recited herein is intended to include all sub-ranges subsumed therein (unless expressly indicated otherwise) and accordingly, the disclosed numeral ranges include every individual value between the minimum and maximum values of the numeral ranges.

The above-mentioned steps constructing the method disclosed in the present disclosure may be performed in a proper order unless explicit conditions state otherwise. However, the scope or spirit of the present disclosure is not limited thereto. All examples described herein or the terms indicative thereof ("for example," etc.) used herein are merely to describe the present disclosure in greater detail. Therefore, it should be understood that the scope of the present disclosure is not limited to the example embodiments described above or by the use of such terms unless limited by the appended claims.

Also, it should be apparent to those skilled in the art that various alterations, substitutions, and modifications may be made within the scope of the appended claims or equivalents thereof.

Therefore, technical ideas of the present disclosure are not limited to the above-mentioned embodiments, and it is intended that not only the appended claims, but also all changes equivalent to claims, should be considered to fall within the scope of the present disclosure.

What is claimed is:

1. A method for providing beauty counseling information, the method comprising:
   generating a first image set including a plurality of first images previously stored based on capturing image information on a periodic basis;
   generating a second image set including a plurality of second images included in the first image set, the second image set being classified based on one or more conditions for providing counseling information;
   calculating a current condition of a body feature of a user based on a comparative analysis of the plurality of second images included in the second image set; and
   in response to an amount of change between the current condition of the body feature and a previous condition of the body feature exceeding a predetermined value, generating beauty counseling information,
   wherein the generating the second image set includes:
   identifying images in the first image set that include a body part that is at least partially nude for providing counseling information based on a degree of obesity; and
   setting the second image set to include the images with the body part,
   wherein the calculating the current condition of the body feature includes:
   separating an area corresponding to a body of the user and an area not corresponding to the body of the user from the plurality of second images in the second image set;
   detecting an edge of the area corresponding to the body of the user; and
   calculating a curvature of the edge,
   wherein the generating the beauty counseling information includes:
   providing beauty counseling information including obesity related information, when an amount of change between the curvature and a previously stored existing curvature exceeds a predetermined value.

2. The method of claim 1, wherein the generating the first image set includes:
   classifying the plurality of first images based on a self-capturing mode in which the user directly captures himself or herself.

3. The method of claim 1, wherein the generating the first image set includes:
   classifying the plurality of first images based on images having same capturing setting information,
   wherein the same capturing setting information includes at least one of brightness, contrast, saturation, color, gamma, exposure, ISO sensitivity, aperture, or shutter speed.

4. The method of claim 1, wherein the generating the first image set includes:
   converting the plurality of first images into converted images having same capturing setting information, wherein the same capturing setting information includes at least one of brightness, contrast, saturation, color, gamma, exposure, ISO sensitivity, aperture, or shutter speed; and
   generating the first image set to include the converted images with the same capturing setting information.

5. The method of claim 1, wherein the generating the second image set includes:
   identifying images in the first image set that include a face of the user for providing counseling information based on a degree of skin aging; and
   setting the second image set to include the images including the face of the user.

6. The method of claim 5, wherein the calculating the current condition of the body feature includes:
   detecting a facial area in the plurality of second images in the second image set; and
   generating skin condition information based on the facial area, the skin condition information including at least one of shine, pores, wrinkles, fine wrinkles, pigmentation, skin redness, or sebum.

7. The method of claim 6, wherein the generating the beauty counseling information includes:
   providing beauty counseling information including skin aging related information, when an amount of change between the skin condition information and previously stored existing skin condition information exceeds a predetermined value.

8. An apparatus for providing beauty counseling information, the apparatus comprising:
   a memory configured to store image information; and
   a controller configured to:
   generate a first image set including a plurality of first images previously stored based on capturing the image information on a periodic basis,
   generate a second image set including a plurality of second images included in the first image set, the second image set being classified based on one or more conditions for providing counseling information,
   calculate a current condition of a body feature of a user based on a comparative analysis of the plurality of second images included in the second image set, and
   in response to an amount of change between the current condition of the body feature and a previous condition of the body feature exceeding a predetermined value, generate beauty counseling information, wherein the controller is further configured to:
identify images in the first image set that include a body part that is at least partially nude for providing counseling information based on a degree of obesity, after generating the first image set,
set the second image set to include the images with the body part,
separate an area corresponding to a body of the user and an area not corresponding to the body of the user from the plurality of second images in the second image set,
detect an edge of the area corresponding to the body of the user, and
calculate a curvature of the edge,
wherein the controller is further configured to:
provide beauty counseling information including obesity related information, when an amount of change between the curvature and a previously stored existing curvature exceeds a predetermined value.

9. The apparatus of claim 8, wherein the controller is further configured to:
classify the plurality of first images based on a self-capturing mode in which the user directly captures himself or herself.

10. The apparatus of claim 8, wherein the controller is further configured to:
classify the plurality of first images based on images having same capturing setting information,
wherein the same capturing setting information includes at least one of brightness, contrast, saturation, color, gamma, exposure, ISO sensitivity, aperture, or shutter speed.

11. The apparatus of claim 8, wherein the controller is further configured to:
convert the plurality of first images into converted images having same capturing setting information, wherein the same capturing setting information includes at least one of brightness, contrast, saturation, color, gamma, exposure, ISO sensitivity, aperture, or shutter speed, and
generate the first image set to include the converted images with the same capturing setting information.

12. The apparatus of claim 8, wherein the controller is further configured to:
identify images in the first image set that include a face of the user for providing counseling information based on a degree of skin aging, and
set the second image set to include the images including the face of the user.

13. The apparatus of claim 12, wherein the controller is further configured to:
detect a facial area in the plurality of second images in the second image set, and
generate skin condition information based on the facial area, the skin condition information including at least one of shine, pores, wrinkles, fine wrinkles, pigmentation, skin redness, or sebum.

14. The apparatus of claim 13, wherein the controller is further configured to:
provide beauty counseling information including skin aging related information, when an amount of change between the skin condition information and previously stored existing skin condition information exceeds a predetermined value.

* * * * *